United States Patent [19]

Parr

[11] Patent Number: 5,769,837
[45] Date of Patent: *Jun. 23, 1998

[54] ABSORBENT ARTICLES WITH INTEGRAL RELEASE SYSTEM AND METHODS OF MAKING SAME

[75] Inventor: Deborah Jean Parr, Plainsboro, N.J.

[73] Assignee: McNeil-PPC, Inc., Skillman, N.J.

[*] Notice: The term of this patent shall not extend beyond the expiration date of Pat. No. 5,217,448.

[21] Appl. No.: 658,919

[22] Filed: May 31, 1996

Related U.S. Application Data

[63] Continuation of Ser. No. 373,913, Jan. 17, 1995, abandoned, which is a continuation of Ser. No. 935,146, Aug. 24, 1992, abandoned, which is a continuation of Ser. No. 568,913, Aug. 17, 1990, abandoned.

[51] Int. Cl.[6] .............................. A61F 13/15; A61F 13/20
[52] U.S. Cl. ...................... 604/390; 604/385.1; 604/386; 604/387
[58] Field of Search .................................. 604/358, 372, 604/385.1, 386, 387, 389, 391

[56] References Cited

U.S. PATENT DOCUMENTS

| | | | |
|---|---|---|---|
| 2,693,439 | 11/1954 | Blanchard et al. | 604/385.1 |
| 3,638,651 | 2/1972 | Torr . | |
| 3,950,824 | 4/1976 | Karami . | |
| 3,994,299 | 11/1976 | Karami . | |
| 4,010,753 | 3/1977 | Tritsch . | |
| 4,024,867 | 5/1977 | Mesek . | |
| 4,040,424 | 8/1977 | Hunt . | |
| 4,085,754 | 4/1978 | Ness et al. . | |
| 4,286,595 | 9/1981 | Ring . | |
| 4,336,804 | 6/1982 | Roeder . | |
| 4,337,772 | 7/1982 | Roeder . | |
| 4,376,440 | 3/1983 | Whitehead et al. . | |
| 4,380,450 | 4/1983 | Reich | 604/386 |
| 4,555,022 | 11/1985 | Eagon et al. . | |
| 4,589,876 | 5/1986 | Van Tilburg . | |
| 4,596,570 | 6/1986 | Jackson et al. | 604/387 |
| 4,608,047 | 8/1986 | Mattingly . | |
| 4,690,680 | 9/1987 | Higgins . | |
| 4,699,792 | 10/1987 | Nick et al. . | |

(List continued on next page.)

FOREIGN PATENT DOCUMENTS

| | | | |
|---|---|---|---|
| 0 182 692 | 5/1986 | European Pat. Off. . | |
| 182 692 A1 | 5/1986 | European Pat. Off. . | |
| 313426 | 10/1987 | European Pat. Off. | 604/387 |
| 313426 A1 | 4/1989 | European Pat. Off. . | |
| 2 086 742 | 12/1971 | France . | |
| 2086742 | 12/1971 | France . | |
| 14 16 936 | 10/1968 | Germany . | |
| 1416936 | 10/1968 | Germany . | |
| 20 49 493 | 4/1971 | Germany . | |
| 2049493 | 4/1971 | Germany . | |
| 3326026 | 2/1985 | Germany | 604/389 |
| 3326026 A1 | 2/1985 | Germany . | |

OTHER PUBLICATIONS

EP 91 11 3865 EPO Search Report.
EP 91 11 3866 EPO Search Report.
EP 91 30 7580 EPO Search Report.
EP 91 30 75 81 EPO Search Report.

*Primary Examiner*—Robert A. Clarke

[57] ABSTRACT

Absorbent articles such as panty liners, thin full-sized sanitary napkins and the like having a garment facing side and a body facing side are provided which may be stored in a folded configuration prior to use. Means of attachment and means of release, most preferably silicone, are created on the garment facing side of the article. The patterns in which the attachment and release means are chosen such that when the article is folded, the adhesive means contact the release means, eliminating the need for release paper, but allowing the article to be unfolded and used. Other embodiments using barrier films affixed to the garment facing side of the article are also disclosed. The barrier films are used in place of an outer wrapper member to protect the body-facing side of the napkins from being soiled prior to use.

14 Claims, 4 Drawing Sheets

U.S. PATENT DOCUMENTS

| | | |
|---|---|---|
| 4,701,178 | 10/1987 | Glaug et al. . |
| 4,725,468 | 2/1988 | McIntyre . |
| 4,781,712 | 11/1988 | Barabino et al. . |
| 4,815,457 | 3/1989 | Mazars et al. . |
| 4,832,008 | 5/1989 | Gilman . |
| 4,862,574 | 9/1989 | Seidy . |
| 4,917,675 | 4/1990 | Taylor et al. . |
| 4,917,929 | 4/1990 | Heinecke . |
| 4,960,417 | 10/1990 | Tarr, Jr. et al. . |
| 4,985,025 | 1/1991 | Lingertat et al. . |
| 5,046,608 | 9/1991 | Laipply . |
| 5,066,289 | 11/1991 | Polski . |
| 5,088,993 | 2/1992 | Gaur . |
| 5,106,383 | 4/1992 | Mulder et al. . |
| 5,133,705 | 7/1992 | Nakanishi et al. ............... 604/389 |
| 5,217,448 | 6/1993 | Glaug et al. . |
| 5,591,153 | 1/1997 | Mattingly, III ............... 604/387 |

ABSORBENT ARTICLES WITH INTEGRAL RELEASE SYSTEM AND METHODS OF MAKING SAME

CROSS-REFERENCES TO RELATED APPLICATIONS

This is a continuation, of application Ser. No. 08/373,913 filed Jan. 17, 1995 (abandoned), which is a Continuation application of Ser. No. 07/935,146 filed Aug. 24, 1992, (abandoned), which is a Continuation application of Ser. No. 07/568,913, filed Aug. 17, 1990 (abandoned), are all incorporated herein by reference.

This application is related to U.S. Ser. No. 07/568,937, filed concurrently herewith, entitled "Absorbent Products Having Optional Side Panel Usage, U.S. Pat. No. 5,217,448 and "Absorbent Articles With Integral Release System and Methods of Making Same", U.S. Ser. No. 568,914 now abandoned".

The present invention relates to improved absorbent articles. More particularly, the present invention relates to sanitary napkins, panty liners and the like having integral adhesives for affixing the absorbent article to a user's undergarment and which do not require an additional wrapping pouch or sheet.

BACKGROUND OF THE INVENTION

Absorbent articles such as panty liners and sanitary napkins are well known throughout the art. Generally, these articles have an absorbent, body facing side and a garment facing side. In many instances, the garment facing side is comprised of a fluid impermeable barrier film. A preferred method of securing these articles so that there is close, direct contact between the perineal area and the user's undergarment is to apply an adhesive to the garment facing side. The adhesive is chosen to provide sufficient anchoring strength to hold the article firmly in place while the user moves.

Inherent in absorbent articles of the above-described construction is the requirement to have release paper applied to the adhesive. The release paper allows the article to be manufactured, packaged, stored, and otherwise handled without the adhesive adhering to itself or any other object. Release paper also serves to prevent oxidation, dust or dirt contamination of the adhesive and evaporation of tackifying resins. Unfortunately, the use of release paper is undesirable for several reasons. First, before the absorbent article can be used, the paper must be removed and discarded. This presents disposal problems and reduces the discretion with which the absorbent articles may be used. Second, release paper adds significantly to product cost. This is particularly true for low cost panty liners and the like which use very little absorbent material. Extra costs due to the release paper are incurred by both the additional material costs and the additional processing time and labor required to apply the release paper.

Related patent application U.S. Ser. No. 08/568,937, entitled "Absorbent Articles Having Integral Release Means and Methods of Making Same", W. B. Mattingly (Attorney Docket No. PPC 325) describes products without release paper ad methods of making such products. The products described therein may be folded in many ways. Consumers generally desire that such sanitary protection products be stored such that the body-facing layer is protected from the environment and maintained in a clean condition prior to use.

In recent years, manufacturers of sanitary protection and adult incontinence devices have provided an outer wrapping member surrounding these devices in storage. This wrapping member aids in the protection of the device from dirt and dust. Furthermore, it provides a discrete means for carrying devices in women's purses such that the devices are not damaged or crushed when transported. However, providing a protective wrapping member may have certain disadvantages. For example, the wrapping member is a separate, large piece of material which must be discarded after removing the sanitary protection device. Although the wrapping member may be utilized to wrap a used sanitary napkin, at times, there may not be a need to wrap a napkin. Furthermore, such wrapping members are often composed of non-biodegradable plastic films. The disposal of such films is difficult and may be wasteful and damaging to the environment.

Thus, it would be desirable to eliminate the need for release paper while still retaining the adhesive applied to the garment facing side of an absorbent article so that it can be used to adhere the absorbent article to the undergarment during use but will not stick to itself or an inappropriate surface before use. It would also be desirable to eliminate the use of a barrier material while retaining the ability to wrap and protect the absorbent article during transport.

SUMMARY OF THE INVENTION

Accordingly, it has now been found, in accordance with this invention and with copending patent application Ser. No. 07/568,397 (Mattingly), that the need for release paper may be eliminated using the method and products of this invention. Moreover, the need for an outer, separate wrapping member has also been eliminated.

More particularly, the elimination of release paper may be accomplished by creating release zones and attachment zones at the extreme longitudinal ends of the undergarment-facing side of the products of this invention in such a pattern that the release zones and attachment zones alternate in placement on the undergarment-facing side. Within the attachment zones are located attachment means. Within the release zones are located release means. The attachment and release means are placed such that when the subject absorbent article is folded along a fold line adjacent the longitudinal ends of the undergarment-facing side of the pad, the attachment means meet with the release means.

The elimination of the outer wrapping member may be accomplished by extending the sides of the undergarment-facing side of the absorbent article sufficiently to permit them to be sealed and perforated. The creation of attachment and release zones on the undergament-facing side of the absorbent article permits its folding and adherence so as to enable the article to remain in this position until use without the need for an outer wrapping member separate from the article itself.

In accordance with this invention, absorbent articles, such as panty liners and the like, are provided which are capable of being stored in a folded configuration prior to use. These absorbent articles have a body-facing side and a garment-facing side. Preferably, attachment zones and release zones are created on the garment facing side of the article. Release means may be created by depositing a release agent within the release zone, e.g., by coating at least a portion of the release zone with a release agent. Most preferably, the release agent is silicone, although it may be any of a number of chemical release agents known to those skilled in the art. However, a release agent need not be deposited to create the release means. Alternatively, the release means may simply constitute designated areas of the garment-facing side of the absorbent article when the garment-facing side of the absorbent article is made of an appropriate material which can act as a release means.

Attachment means are preferably created on the garment facing side of the article by delineating attachment zones and depositing attachment or adhesive means to at least a portion of the attachment zones. These attachment zones may be treated to make them more receptive to the attachment means. The attachment means may consist of any means of releasably attaching the absorbent article known to those skilled in the art, for example, pressure-sensitive adhesives, Velcro or non-slip materials or the like. For the sake of clarity, the following descriptions will exemplify embodiments employing pressure-sensitive adhesive attachment means, however, the description will apply equally to other attachment means.

The patterns in which the adhesive and release means are applied are chosen so that when the article is folded, the attachment means contact the release means, eliminating the need for release paper, but allowing the article to be unfolded and used. Advantageously, according to this invention, the absorbent articles may be folded such that the garment-facing side can shield the body-facing side from exposure to the elements during storage and prior to use. The garment-facing side can be extended beyond the longitudinal edges of the article, sealed and perforated for ease in use. This configuration protects the body-facing side of the article while eliminating an extraneous sheet of material.

The products of this invention preferably contain at least one attachment zone proximate to the transverse ends of the central absorbent. The products of this invention are folded across at least three transverse fold lines in order to provide complete coverage of the interior body-facing side of the absorbent. One of the fold lines may be a transverse central fold line, with two other fold lines spaced approximately equally between the transverse central fold line and the transverse ends of the absorbent article. However, the fold lines may be spaced such that two transverse fold lines are located approximately one-third of the distance between the transverse ends, with additional transverse folds adjacent the transverse ends. The end-folds would preferably contain attachment means which are releasably attached to the garment-facing side of the absorbent article.

The products of this invention will permit manufacturers to eliminate in their process of manufacture the step of providing an outer wrapping means for absorbent articles. This will aid in simplifying the manufacturing process and will reduce cost of materials and labor.

The garment facing side of the products of this invention on which the attachment and release zones are located may be polyolefin (e.g., polyethylene or polypropylene) films, non-wovens or the like.

Regardless of the type of attachment means used, the attachment means must bond more strongly to the attachment zone than to the user's undergarment and/or to the release means; the release means must bond more strongly to the release zone than it does to the attachment means and/or to the undergarment; and the attachment means must not bond so strongly to the undergarment that it rips or damages the undergarment by depositing adhesive means on the undergarment.

According to the method of making the products of this invention, there is provided an absorbent article which may be folded along at least three fold lines across the transverse axis of the product, which remains in the folded position during storage, opens upon demand and which can be attached to the crotch portion of an undergarment. Furthermore, the method and products of this invention permit the wearer to disengage the article from the undergarment without depositing attachment means on the undergarment or tearing the undergarment or the absorbent article. The garment-facing side of the product may be extended beyond the longitudinal edges of the central absorbent, sealed and perforated at several positions parallel to the longitudinal edges of the absorbent. This will permit the user to choose the ultimate width of the product in use. In addition, the extensions of the garment-facing side of the product may be used as panty crotch edge protectors.

The ability to accomplish the objective of releasably attaching zones of the garment-facing side is achieved by controlling the differential "bond strength" with respect to each surface to which the attachment means and the release means are adhered and by placement of the attachment and release means on the undergarment-facing side of the pad. "Peel strength" is a measurement of the strength of an adherent bond. Peel strength is measured in force per unit of width, i.e., the force required to separate adherently joined materials per unit of width.

Preferably, a high peel or bond strength should be present between the attachment means and the attachment zones on the garment facing side of the articles of this invention. Likewise, a high peel or bond strength should be present between the release means and the release zones on the garment facing side of the articles of this invention.

A relatively lower peel strength should be present between the release means and the attachment means such that they may be separated prior to use. The differential peel strengths permit the articles of this invention to be stored in a folded position, opened at will without damaging the absorbent article and adhered to an undergarment without damaging the undergarment or absorbent article upon removal.

DETAILED DESCRIPTION OF THE PREFERRED EMBODIMENTS

Figure 1:
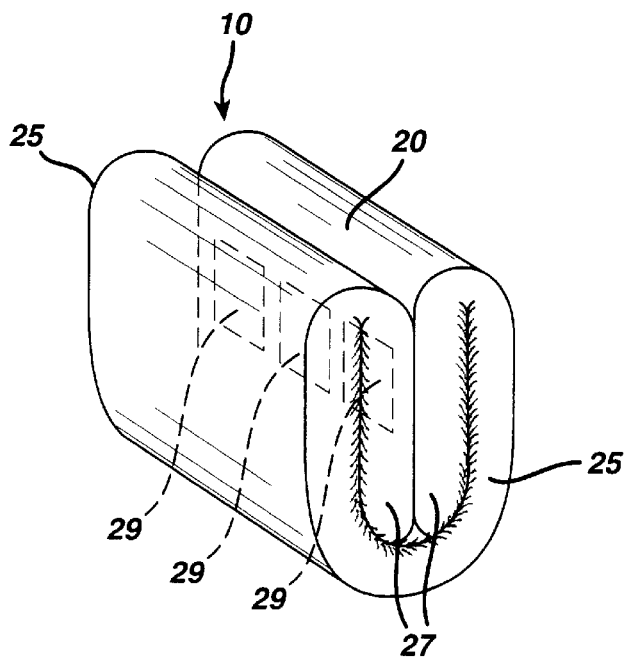
FIG. 1 is a perspective view of a panty liner made in accordance with the present invention.

The present invention eliminates the need for release paper by providing release means and attachment means in the respective release and attachment zones delineated on the garment-facing side of an absorbent article. The placement of the attachment and release zones at the extreme longitudinal ends of the undergarment-facing side of the pad permits the symmetrical attachment of the pad in use. Alternating the attachment and release zones transversely across the pad allows placement of attachment means at both extreme ends of the pad, thus providing attachment utility at both ends in the undergarment. The pad will not therefore, disengage itself from the undergarment at either end during use.

According to one preferred embodiment, the attachment means are in the form of an adhesive coating. In this embodiment, the release means should have a low enough peel strength with respect to the adhesive coat so as to separate from the adhesive coat without causing damage by stripping adhesive from the attachment zones. The adhesive coat used should have a high enough peel strength with respect to the attachment zone of the garment facing side of the absorbent article to provide sufficient anchorage to prevent adhesive transfer from the article to the undergarment when removing the product from the undergarment after use.

Most preferably, the zones of release and attachment are chosen so that when the product is folded, the adhesive means applied in an attachment zone is covered by the release means within a release zone.

A number of methods may be used to impart the required peel strength characteristics to different zones on the garment facing side of an absorbent article. One method is to use a coating of silicone release agent as the release means applied in the release zones. The attachment zones are left untreated with the silicone coat, and adhesive is applied to at least a portion of the untreated areas. Preferably, the release means are larger in area than the adhesive means such that the adhesive means and release means have a tolerance available for slight folding errors or means placement errors. Preferably, an area of the attachment zones peripherally surrounding the area to which the adhesive is applied may be left uncovered by adhesive. This creates a space around the adhesive such that when the panty liner is folded, there is some tolerance within which the areas of adhesive can avoid contacting the other adhesive means. Furthermore, this provides tolerance for slight errors in adhesive placement within the attachment zone.

Many types of barrier films may be used on the undergarment-facing side of the absorbent to create or allow the creation of attachment and/or release means on that side of the absorbent. For example, the barrier film may be made of polypropylene, high density polyethylene, low density polyethylene, linear low density polyethylene, cellophane, Polyvinyl acetate, polyvinyl alcohol, polycaprolactan, polyester, polytetrafluoroethylene (Teflon®), or mixtures or coextrusions of one or more of these materials. Additionally, films made of materials synthesized to facilitate high moisture vapor transmission could also be used. Highly calendered paper or nonwoven material may also be substituted for films. For example, nonwoven polyester, polyethylene, rayon and/or cotton or blends thereof may be used as barriers. Rayons, cottons, or other fibrous nonwovens known to those of ordinary skill in the art to be hydrophilic, should be treated to be fluid repellant. Fluorocarbon materials, silicone and the like may be used to render such materials fluid repellant. Further, additives may be combined with the film resin to control the peel or bond strength of the film-to-adhesive bond.

In addition to the above, certain materials, such as Teflon®, produce inherently low adhesive-to-film peel strengths. For these materials, a release coating may not be required in the release zones. Instead, treatment may be necessary to increase the adhesive-film bond in the zones to which adhesive is to be applied. A low-peel strength substrate may be embossed to provide more anchorage surface for the adhesive, or selectively corona treated. The zones to which adhesive will be applied could be either chemically etched or altered to otherwise impart a stronger adhesive-film bond in the attachment zone. In certain embodiments, the adhesive can be applied at a temperature high enough to partially melt the film and produce a "weld" between the film and the adhesive, thereby obviating the need for a separate treatment.

A preferred method of surface treatment is corona treatment of the barrier film which forms the garment facing side of the absorbent article. Corona treatment involves the application of a large voltage across the surface of the film. The resulting treated surface is very reactive and permits the film to form chemical, as well as mechanical, bonds with coatings applied to the surface of the treated article. This provides firmer attachment of both the adhesive and the silicone release coating to the barrier film.

For purposes of securing the absorbent product to the user's undergarment, a wide variety of positioning adhesives are available, pressure sensitive hot melt adhesives being the most widely used and most preferred. These adhesives may be A-B-A block copolymers or the like, such as styrene-ethylene-butylene-styrene block copolymer, e.g., Stereon, or a diblock AB styrene butadiene adhesive. Hot melt adhesives such as HM-6513 or 1972 from H. B. Fuller (St. Paul, Minn.) or N.S. 34-5509 from National Starch (Bridgewater, N.J.) are good candidates. Of course, adhesives other than hot melt adhesives may also be used and should be chosen based on the numerous factors such as the compatibility of the adhesives with the other materials being used and the end use of the absorbent product.

The products of this invention may also be made by providing a roll of film which is coated with silicon on one side and adhesive on the other. Strips of this silicone-coated "tape" may be placed on one side of another film which has adhesive on both sides. The tape can be placed in an appropriate pattern (silicone side exposed) against the double adhesive coated film so that the adhesive of one side meets adhesive of the other. This will bond the tape to the film and produce areas of silicone release on the film, i.e., release means. The areas not covered with the tape become the attachment means. Patterns of release and attachment means can be configured such that, when folded, the attachment means is covered by release means.

The absorbent article of this invention may contain an out nonwoven material as a garment-facing material, which has attachment and release zones as well as a sheet of film or fabric which is located between the garment-facing material and the inner central absorbent layers. This film or fabric may extend beyond the transverse width of the garment-facing material and the central absorbent and may be sealed in order to enclose the body-facing side of the absorbent article during storage, in place of sealing the garment-facing material. This would permit the garment-facing material and sealing layer to be constructed of different types of materials.

FIG. 1 illustrates one of the preferred embodiments of the product of this invention. Panty liner 10 has two transverse edges 25 and two longitudinal edges 27. Panty liner 10 also has one or more areas of attachment 29 which serve to maintain panty liner 10 in a folded configuration prior to use.

Figure 2:
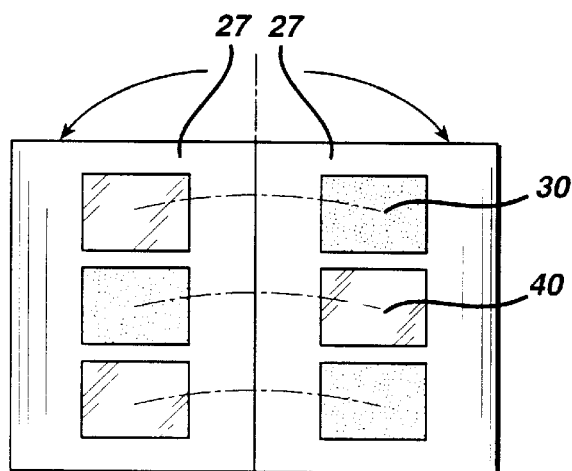
FIG. 2 is a plan view of the garment-facing side of the panty liner of FIG. 1, which has been partially opened.

FIG. 2 illustrates the embodiment depicted in FIG. 1 after it has been partially opened. In this view, the actual areas in which attachment means 30 and release means 40 are located can be seen. Choosing the patterns of attachment means 30 and release means 40 on garment-facing side 20 of the panty liner so that they will contact each other when the article is folded eliminates the need for release paper on the garment facing side of panty liner 10. Release means 40 must completely cover attachment means 30. Thus, as shown in FIG. 1, each attachment means 30 is placed in an alternating pattern with a release means 40 arranged along the longitudinal ends 27 of the liner such that the attachment means 30 cannot register with each other.

Figure 3:
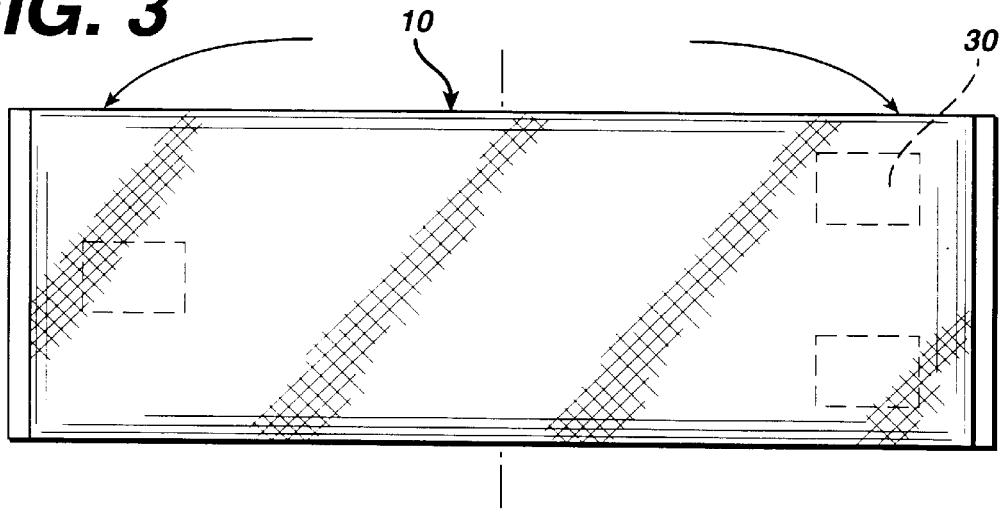
FIG. 3 is a plan view of the body-facing side of the panty liner depicted in FIG. 1.

FIG. 3 depicts panty liner 10 of FIGS. 1 and 2 as it appears when fully opened. Once panty liner 10 is fully opened, attachment means 30 are available for use in attaching the liner to the undergarment of a user.

Figure 4:
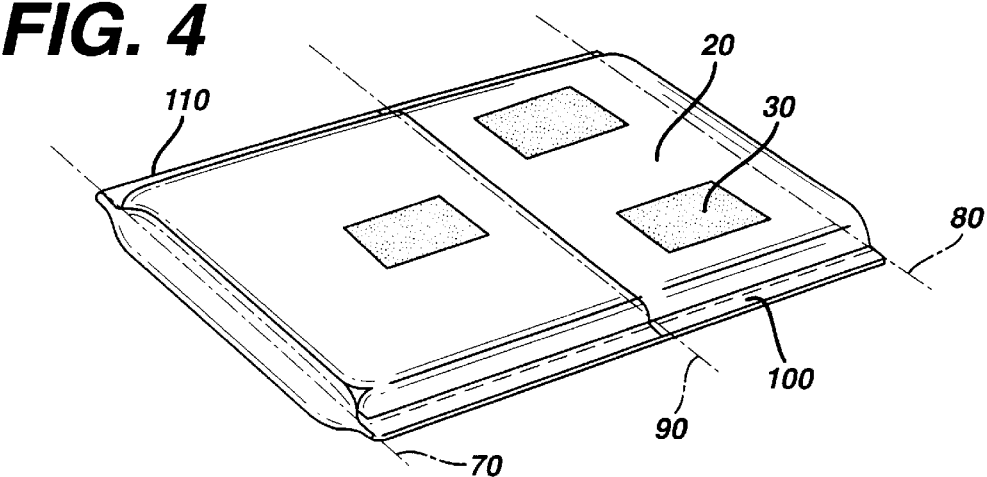
FIG. 4 is a perspective view of an alternative embodiment of a panty liner made in accordance with the present invention in a partially folded condition, prior to use.
Figure 5:
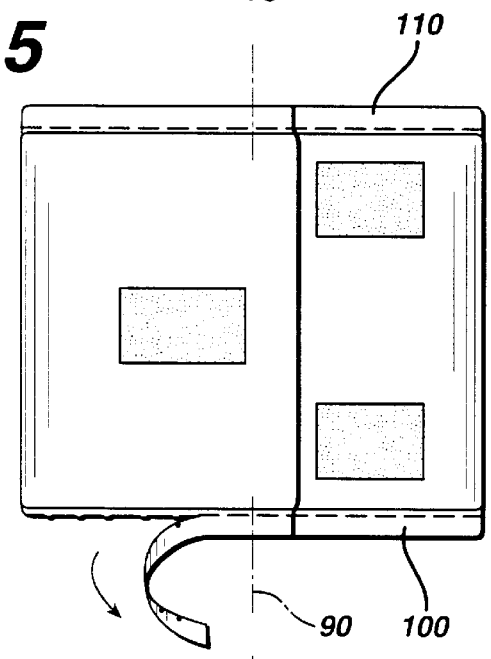
FIG. 5 is a plan view of the alternate embodiment of the panty liner depicted in FIG. 4, illustrating the removal of the perforated portion of peripheral sealed material.
Figure 6:
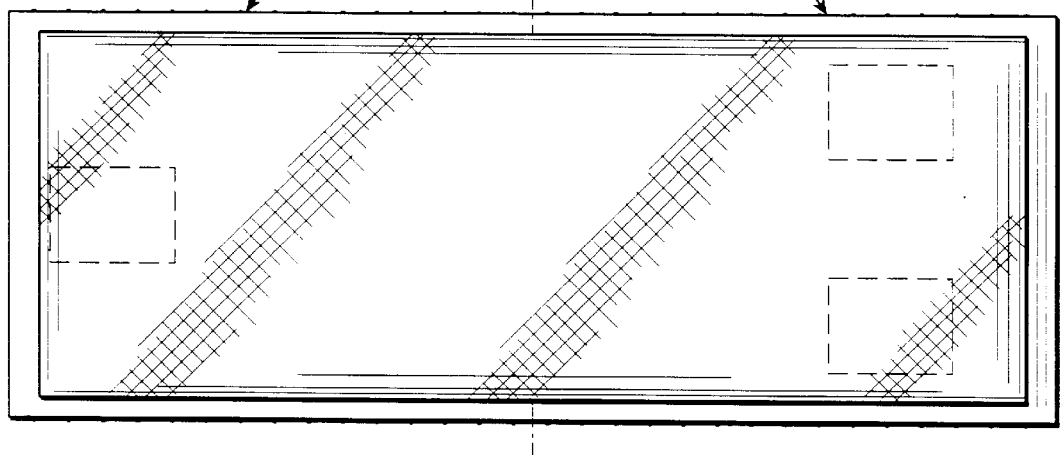
FIG. 6 is a plan view of the body-facing side of the embodiment of FIGS. 4 and 5, fully opened.

An alternate embodiment of the present invention is illustrated in FIGS. 4–6. In this embodiment, adhesive means 30 are applied to a panty liner 10 along its longitudinal ends. However, the entire surface of the garment-facing side 20 of the panty liner serves as a release surface. The liner is folded along three transverse axes: about one-quarter of the way from each longitudinal end and along the transverse central axis. In production, this embodiment may be made such that the transverse fold lines 70 and 80 are made prior to making a fold at 90. Before folding the liner at 90, the excess material along the longitudinal edges of the napkin 100 and 110 are sealed mechanically, adhesively or thermally and perforated. The liner may then be adhered using adhesive means 30. The user of panty liner 10 may then open the pad by releasing the adhesive means, tearing off the perforated sections 100 and 110 and unfolding the remainder of the liner.

Adhesive means 30 are then available, as depicted in FIG. 6, to adhere the liner to the undergarment of the user.

Perforated sections 100 and 110 may be extended in the transverse direction such that they are considerably wider than the transverse width of the central absorbent pad. They may be perforated in several places along the longitudinal axis of the pad. Thus, the user may tear off the amount of material necessary to conform the size of the side extensions to her wishes. Such side extensions may serve as panty protectors to guard the edges of the crotch section of the user's undergarments during use.

Figure 7:
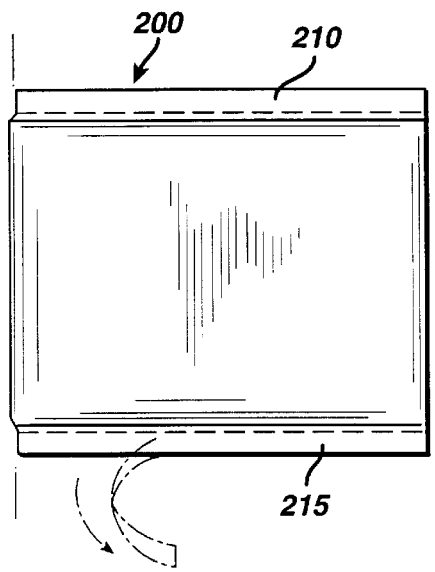
FIG. 7 is a plan view of a folded alternative embodiment of an absorbent article according to this invention.
Figure 8:
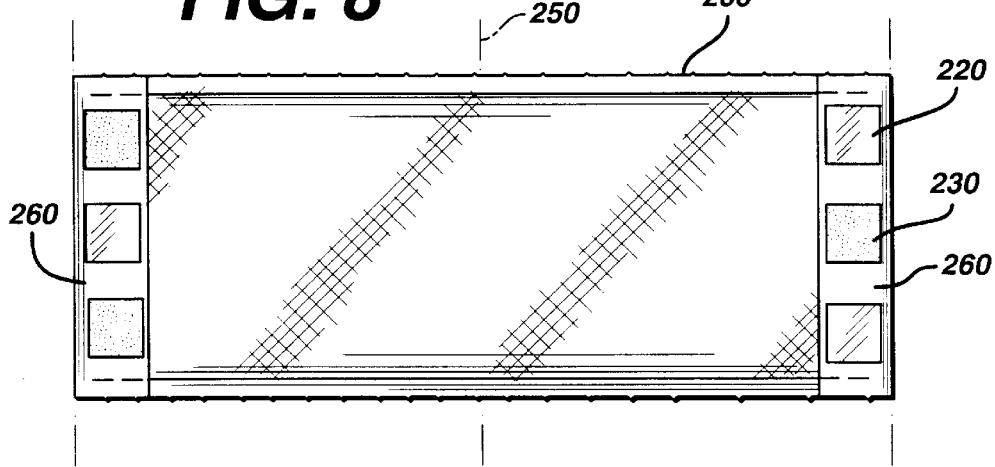
FIG. 8 is a plan view of the garment-facing side of the embodiment depicted in FIG. 7.
Figure 9:
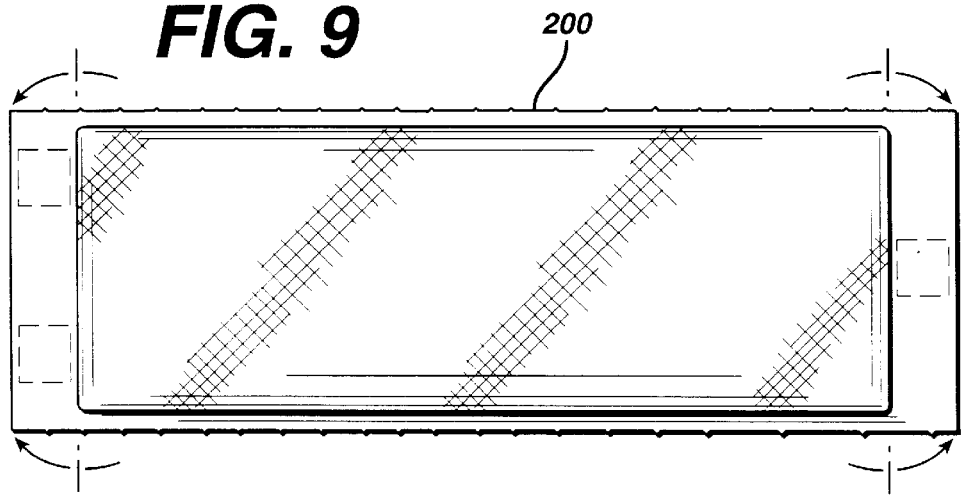
FIG. 9 is a plan view of the body-facing side of the embodiment depicted in FIGS. 7 and 8.
Figure 10:
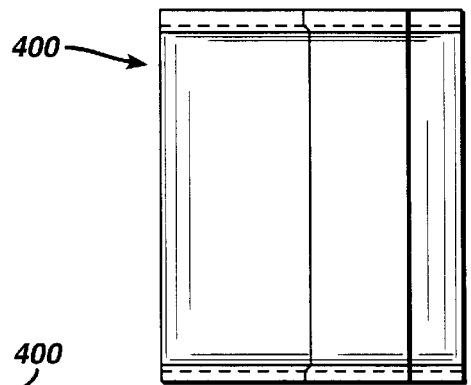
FIG. 10 is a plan view of a folded alternative embodiment of an absorbent article according to this invention.
Figure 11:
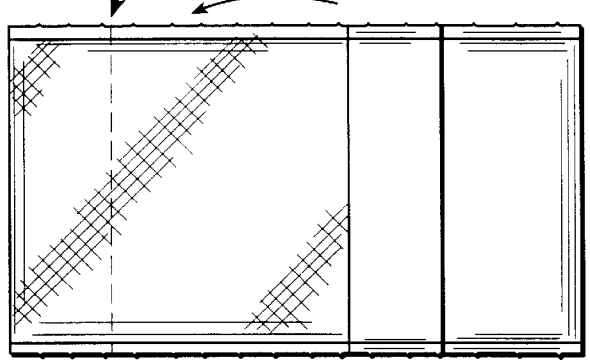
FIG. 11 is a plan view of the partially-opened article depicted in FIG. 10.
Figure 12:
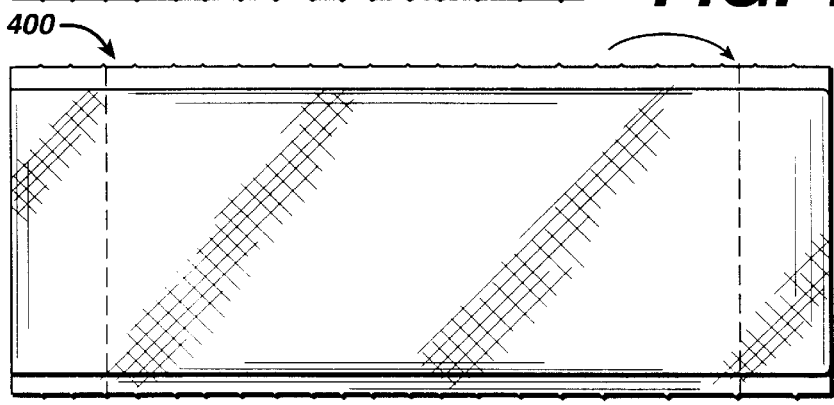
FIG. 12 is a plan view of the further-opened article depicted in FIGS. 10 and 11.
Figure 13:
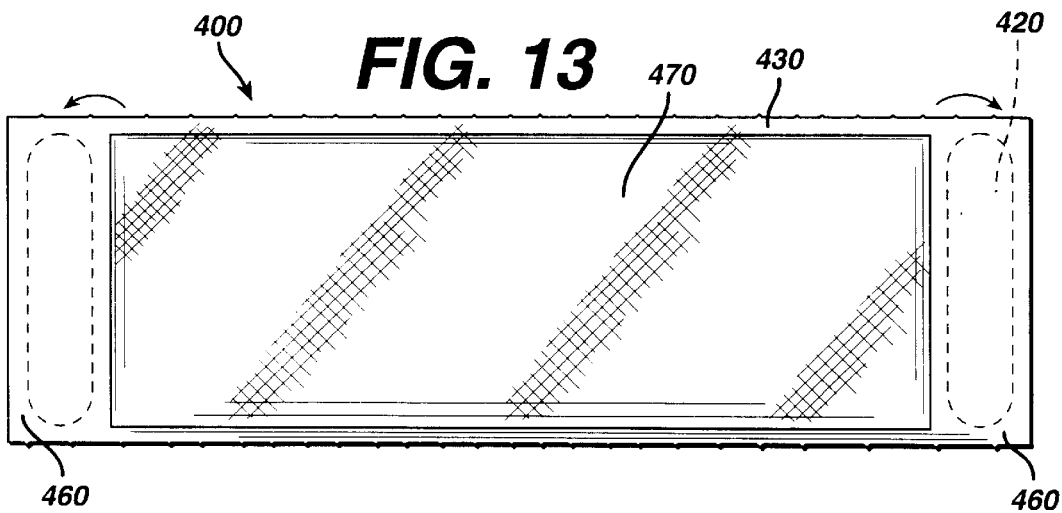
FIG. 13 is a plan view of the fully-opened article depicted in FIGS. 10, 11 and 12.

FIGS. 7, 8 and 9 illustrate another preferred embodiment of the products of this invention. In this embodiment, sanitary napkin 200 is intended to be folded along transverse central fold line 250 and the excess material along the longitudinal edges 210 and 215 sealed and perforated. Adhesive means 220 and release means 230 are located on flanges 260 at the ends of pad 200. Flanges 260 are folded toward transverse central fold line 250 prior to sealing and perforating the longitudinal edges, as shown in FIG. 8. When the pad is folded along line 250, adhesive means 230 and release means 220 contact one another and releasably adhere the pad into a closed position. Upon opening, flanges 260 may be opened away from the body-facing side of the pad and used to attach the pad to the undergarment of the user.

FIGS. 10, 11, 12 and 13 represent yet another embodiment of the sanitary napkins of this invention. In accordance with this embodiment, flanges 460 are extensions of the garment-facing side of pad 400. Adhesive means 420 are applied to flanges 460. Either release means 430 are created on the garment-facing side of the pad or the garment-facing side of the pad is made of a barrier that is able to serve as a release surface. Adhesive means 420 are folded away from the body-facing side of the pad 470 toward release means 430 and the pad may then be folded in thirds, the longitudinal ends sealed and perforated.

Before use, a panty liner or other absorbent article may be stored in a folded configuration. Thus, in a preferred embodiment of the articles of this invention, the products of this invention are folded along one or more fold lines and the release and attachment means brought together into contact with each other. The attachment means register with, or contact only, the release means when the panty liner is folded. No area of the attachment means applied to or located within the attachment zones may contact other attachment means on the garment facing side of the article. If the attachment means contacted one another, the user would be unable to unfold the article without difficulty. When the article is unfolded just prior to its application to the undergarment, the attachment means are exposed to the undergarment surface to which they will be affixed.

Although three embodiments of the present invention have been illustrated and described in detail, the present invention is in no way so limited. One of ordinary skill will immediately appreciate that the present invention has application to numerous other absorbent articles in addition to the panty liner illustrated. Moreover, the present invention may also be used to eliminate release paper from absorbent articles which are folded along one or more fold lines including those other than the transverse central fold-line.

There are a variety of methods by which the absorbent products of this invention may be made. Preferably, an appropriate barrier film is first printed with a silicone release coating in the release zone. The release coating is cured and adhesive is applied to the attachment zones disposed on the same side as the silicone. Adhesive is also coated on the absorbent facing side of the barrier film to help laminate the film to the absorbent. The adhesive in the attachment zones is preferably applied so as not to occupy the entire surface area of the attachment zones. This provides a tolerance for slight errors in placement of the attachment means in the attachment zone while still substantially guaranteeing the attachment means will lie entirely within the attachment zone. The attachment means is preferably smaller in area than the release means. This allows a tolerance for slight errors in folding the product while substantially guaranteeing the attachment means will be covered by the release means.

The latter side is then affixed to an absorbent substrate, leaving the release coating and adhesive exposed to form the garment facing side of the absorbent article. The finished article is then folded along at least one fold line. The release means and adhesive means contact each other so that the article may be unfolded prior to use without the adhesive means bonding to itself or to the barrier film. The release means may overlap, but the adhesive means must substantially contact only the release means.

For many barriers, treatment is preferred in most cases to impart a low-peel strength surface in the release zones.

Silicone-based release agents are excellent for this purpose; these compounds can be applied using many processes other than the screen print/ultraviolet cure set forth below in the Example. In addition to silicon-based release agents, other types of release coats may be used including paraffin waxes, non-stick coatings, varnishes and others known to those of skill in the art. Some types of adhesives become non-tacky when dried or cooled (such as non-pressure sensitive hot melt adhesives or cold glues) and may make suitable release means if used as a coating in the release zone.

Various silicone curing methods may be used, including in addition to ultraviolet curing, heat curing or electron beam curing. The release coating may be applied using a wide variety of coating equipment. Direct and reverse gravure coaters, three-roll offset coaters, smooth five-roll coaters, or ink jet printing are just a few of the possible equipment types contemplated for use in the present invention.

The following Example further illustrates the preferred embodiments of the present invention:

EXAMPLE

A panty liner according to this invention may be made as follows. A roll of barrier film of 1.5 mil white microembossed polyethylene film Type #EMB533 available from Exxon Corporation, is first slit to about a 6.125" width. The film is then corona treated to have a surface energy of about 38 dynes/cm on the side which is to be coated. Silicone is then printed on the corona-treated side in the configuration shown in FIG. 1. The silicone may be printed using a screen printer manufactured by Kraemer Koating, Inc. (Serial No. 1036, Toms River, N.J.). An ultraviolet (UV) curable type silicone release agent may be used, which is made by the General Electric Corporation. The formula is as follows:

| Percent | Product # | Description |
| --- | --- | --- |
| 98% | UV9300* | UV-curable silicone |
| 2% | UV9310C* | UV-activated catalyst |

*General Electric Product Designations

The silicone release agent is added behind a doctor blade inside the printing screen using a low volume metering pump, such as the variable speed pump manufactured by Ismatec. (Model No. 7617-60, made in Switzerland by ISMATEC SA, Zurich, Switzerland). A printing screen which may be used is made by New England Rotary Screen, Inc. (Fall River, Mass.). A 125 mes Pantene screen has been found to produce an even coating. The coat weight of the silicone should be about 3.4 grams/meter$^2$(g/m$^2$). It should be noted, however, that the added coating weight can be reduced greatly with more carefully designed equipment. Ideally, only enough silicone should be applied to impart consistent release characteristics to the coated area.

The silicone release material is then cured using the Mini-Conveyorized UV Curing System from American Ultraviolet Company (Murray Hill, N.J.). A lamp setting of 300 watts/inch provides adequate curing over a wide range of speeds, up to almost 400 feet/minute. The optimum machine speed using the materials and equipment of this Example is about 200 feet/min. The curing step fixes the silicone in the release zone thereby preventing transfer of silicone to the adhesive means.

After the silicone is printed and cured onto the barrier film, adhesive may be applied. The adhesive is applied within the attachment zones. Preferably the adhesive is not applied to the entire area of the attachment zones. Applying adhesive means onto a smaller area than the whole of the attachment zone, makes registration of the adhesive means easier within the attachment zone. Generally, creating release means which is larger than the adhesive means area is preferred, because this allows for folding error tolerance.

In this Example, the adhesive is applied after the silicone coating, on a separate adhesive coating apparatus. Yet, both the silicone release coating and adhesive could be applied in sequence on the same machine. The adhesive used in this example is HM-1972 hot melt adhesive from H.B. Fuller Company (St. Paul, Minn.). The adhesive is applied at a coating weight of about 71 mg/inch in three zones. Lower coating weights may also be used as long as there is an amount of adhesive sufficient to hold the product in place during use. For the application of this Example, these strips are about one-half inch wide, about 1.6 inches long and separated by about 0.9 inch spaces between them. The adhesive is applied to release paper and transferred to the film, the release paper being left in place to aid in rewinding the coated film. The head of the adhesive nozzle is fashioned to produce all adhesive areas at once. The head is alternately turned on and off to provide enough space between the sets of adhesive areas to fashion individual products.

In order to affix the barrier film to an absorbent core or substrate, the same adhesive may be sprayed onto the absorbent-facing side of the barrier film to be used as a laminating adhesive. The adhesive may also be extruded onto the absorbent-facing side of the barrier film. Release papers are used to cover the laminating adhesive as well to aid winding the barrier film into rolls. The release papers are discarded when the product is assembled. Release papers are needed here only by virtue of the manual process herein described. No processing release paper would be required if all the steps of the process are performed on the same machine.

The laminating adhesive is then exposed by removing the release paper and an absorbent batt is placed against the laminating adhesive. For this Example, the absorbent core or substrate is a co-form of pulp and thermoplastic fiber substantially similar to that used in the CAREFREE PANTY SHIELDS® brand of panty liners manufactured by Personal Products Company of Milltown, N.J. The absorbent is fashioned as a 4.25" width material C-folded around a 1.8 inch insert of the same material. The final width dimension of the absorbent is approximately 2.0". The composite of barrier and absorbent is then crimped on the ends using a knurled block which is hot pressed into the product ends. The product ends are then cut to provide a rounded tab end.

The remaining release paper which covers the adhesive applied to the garment facing side is then removed and the article may be folded in half, in thirds or in quarters, as illustrated in the accompanying FIGURES. The adhesive means contact the spots of release coating, allowing the product to be easily unfolded without damage or the need to discard a release paper.

The present invention is not limited to the Example and embodiments set forth above. As will be understood by those of ordinary skill in the art, alternate embodiments, variations and modifications of the present invention are possible.

Accordingly, reference should be made to the appended claims to ascertain the full scope of the present invention.

What is claimed is:

1. A absorbent article capable of being affixed to a user's undergarment, having a body facing side and a garment facing side, transverse ends and longitudinal edges, wherein the body facing side comprises an absorbent core and the garment facing side comprises at least one attachment zone comprising attachment means located proximate to the transverse ends of the absorbent article and at least one release zone comprising release means, said attachment means and said release means being attached to said garment facing side with a bond, and at least three fold lines along which said article may be folded such that the attachment means contacts the release means, thereby forming a releasable bond between said attachment means and said release means, whereby said release means protects the attachment means prior to use, and whereby the garment facing side substantially shields the body facing side, the strength of the bond between said release means and said garment facing side being greater than the strength of the bond between the release means and said attachment means.

2. An absorbent article capable of being affixed to a user's undergarment, having a body facing side and a garment facing side, wherein the body facing side comprises an absorbent core having longitudinal edges and transverse ends, and the garment facing side comprises (i) a substrate (ii) at least one attachment zone and (iii) at least one release zone, said attachment zone comprises attachment means located proximate to the transverse ends of the absorbent article, said release zone comprises release means, said attachment means and said release means being attached to said garment facing side with a bond, and at least three fold lines along which said article may be folded such that the attachment means contacts the release means, thereby forming a releasable bond between said attachment means and said release means, whereby said release means protects the attachment means prior to use, and whereby the garment facing side substantially shields the body facing side, said substrate extending transversely beyond the longitudinal edges of the absorbent core thereby forming an extension of said substrate extending from each longitudinal edge, said extension of said substrate being sealed along the peripheral edge of said extension and perforated between said peripheral edge of said extension and said longitudinal edge of the absorbent core.

3. A panty liner capable of being attached to an undergarment when used and having transverse ends, comprising:

(a) an absorbent core having a body facing side and a garment facing side;

(b) a fluid impervious barrier film forming at least a portion of said garment facing side of the absorbent core, said barrier film having at least three fold lines disposed thereon;

(c) adhesive disposed on a portion of the garment-facing side proximate to the transverse ends of the liner for adhering said liner to an undergarment during use;

(d) a release coating non-releasably bonded to a portion of said garment facing side;

(e) means for retaining said liner in a folded state along said fold lines during storage and for releasing said liner from said folded state prior to use, whereby said body-facing side is protected during storage, said means for retaining and releasing said liner from said folded state comprising said adhesive and said release coating being disposed on regions of said garment facing side which contact each other when said liner is folded along said fold lines, whereby said adhesive retains said liner in the folded state during storage, but releases from said release coating when said liner is unfolded prior to use.

4. An absorbent article capable of being affixed to a user's undergarment, having a body facing side and garment facing side, transverse ends and longitudinal edges, wherein the body facing side comprises an absorbent core and the garment facing side comprises at least one attachment zone comprising attachment means located proximate the transverse ends and at least one release zone comprising release means, said attachment means being attached to said garment facing side with a bond, and at least three fold lines along which said absorbent core is folded such that the attachment means contacts the release means, said release means being non-releasably attached to said garment facing side and releasably attached to the attachment means, whereby the release means protects the attachment means and the garment facing side substantially shields the body facing side.

5. An absorbent article according to claim 4, wherein said attachment means is completely covered by said release means.

6. The absorbent article of claim 4, wherein said absorbent article has the shape of a rectangle.

7. The absorbent article of claim 4, wherein one of the fold lines along which the absorbent core is folded is a central transverse fold-line.

8. The absorbent article of claim 4, wherein the core may be folded about a central transverse fold line and two additional transverse fold lines each located intermediate the central transverse fold line and each transverse end of the article.

9. The absorbent article of claim 4, wherein said attachment means is an adhesive.

10. The absorbent article of claim 9, wherein the adhesive means retain the article in a folded configuration and the release means releases the adhesive means without causing transfer of adhesive from the attachment zone, and leaving the adhesive in such a condition to secure the absorbent article to said user's undergarment.

11. The absorbent article of claim 4 wherein the release means comprises silicone.

12. The absorbent article of claim 4, wherein the garment facing side comprises a fluid impermeable barrier film means.

13. The absorbent article of claim 12, wherein the barrier film means comprises a polyolefin film.

14. The absorbent article of claim 13, wherein the barrier film means comprises a polyethylene film.

* * * * *